(12) United States Patent
Leibinger (10) Patent No.: US 9,186,252 B2
(45) Date of Patent: Nov. 17, 2015

(54) TIBIA IMPLANT FOR TIGHTENING THE PATELLA TENDONS

(75) Inventor: Rita Leibinger, Mühlheim (DE)

(73) Assignee: RITA LEIBINGER GMBH & CO. KG, Neuhausen O.E. (DE)

( * ) Notice: Subject to any disclaimer, the term of this patent is extended or adjusted under 35 U.S.C. 154(b) by 92 days.

(21) Appl. No.: 13/550,039

(22) Filed: Jul. 16, 2012

(65) Prior Publication Data

US 2013/0030540 A1    Jan. 31, 2013

Related U.S. Application Data (60) Provisional application No. 61/511,577, filed on Jul. 26, 2011.

(51) Int. Cl.
| | |
|---|---|
| A61F 2/38 | (2006.01) |
| A61F 5/00 | (2006.01) |
| A61F 2/28 | (2006.01) |
| A61F 2/30 | (2006.01) |
| A61B 17/80 | (2006.01) |

(52) U.S. Cl.
CPC ............... *A61F 2/28* (2013.01); *A61B 17/8061* (2013.01); *A61F 2002/2835* (2013.01); *A61F 2002/2892* (2013.01); *A61F 2002/3092* (2013.01); *A61F 2002/30576* (2013.01); *A61F 2002/30841* (2013.01); *Y10T 29/49908* (2015.01)

(58) Field of Classification Search
CPC .... A61F 2/389; A61F 2002/3092–2002/3093; A61F 2002/30771; A61F 2002/2835; A61F 2002/30576; A61B 17/8095; A61B 17/809

USPC .............. 623/20.3, 23.29, 23.3, 23.32, 23.5, 623/23.53–23.55, 23.28, 16.11
See application file for complete search history.

(56) References Cited

U.S. PATENT DOCUMENTS

| | | | | |
|---|---|---|---|---|
| 5,766,251 | A * | 6/1998 | Koshino | 623/11.11 |
| 6,086,593 | A | 7/2000 | Bonutti | |
| 6,409,767 | B1 * | 6/2002 | Perice et al. | 623/21.18 |
| 6,432,106 | B1 * | 8/2002 | Fraser | 623/17.11 |
| 8,388,690 | B2 * | 3/2013 | Singhatat et al. | 623/23.51 |
| 8,430,930 | B2 * | 4/2013 | Hunt | 623/17.11 |
| 2005/0177245 | A1 * | 8/2005 | Leatherbury et al. | 623/23.5 |
| 2010/0076564 | A1 | 3/2010 | Schilling et al. | |
| 2011/0313532 | A1 * | 12/2011 | Hunt | 623/18.11 |

FOREIGN PATENT DOCUMENTS

| | | |
|---|---|---|
| DE | 32 24 265 A1 | 1/1984 |
| DE | 696 37 048 T2 | 5/1998 |
| DE | 102005037141 | 2/2007 |
| DE | 102006047663 | 4/2008 |
| FR | 2887760 A1 | 1/2007 |
| WO | WO 2012/106323 A1 | 8/2012 |

* cited by examiner

*Primary Examiner* — Thomas J Sweet
*Assistant Examiner* — Brian Dukert
(74) *Attorney, Agent, or Firm* — Henry M. Feiereisen LLC (57) ABSTRACT

A tibia implant for tightening the patella tendons, has a vertical cross section which in mounted position tapers downward, an essentially vertically arranged base plate which carries a sponge structure, wherein the sponge structure on both sides rests against a respective vertical cut surface of a vertical knee proximal incision of the tibia.

22 Claims, 7 Drawing Sheets

TIBIA IMPLANT FOR TIGHTENING THE PATELLA TENDONS

CROSS-REFERENCES TO RELATED APPLICATIONS

This application claims the benefit of prior filed U.S. provisional Application No. 61/511,577, filed Jul. 26, 2011, pursuant to 35 U.S.C. 119(e), the disclosure of which is incorporated herein by reference.

BACKGROUND OF THE INVENTION

The present invention relates to a tibia implant for tightening the patella tendons The following discussion of related art is provided to assist the reader in understanding the advantages of the invention, and is not to be construed as an admission that this related art is prior art to this invention.

From US 2010/0076564 an implant has become known with which in particular in the veterinary medicine the tendons of a knee can be tightened again. For this, the tibia is split from above in the knee proximal region so that a wedge shaped incision is created. However, the tibia section must not be cleaved off completely. The implant is inserted into the incision so that the tibia section is braced toward the front. The implant is a wire frame which is constructed in the manner of a conductor path structure and is flexible with regard to the wedge angle. After inserting the implant into the tibia incision the implant is bent upwards until the side surfaces of the implant rest against the cut surfaces of the incision. Bending of fastening loops out of the plane of the cut surfaces in the direction of the outer surface of the tibia and the tibia section can now allows fastening the implant to the tibia by means of screws.

However, it has proven disadvantageous in this case that the implant is much too filigree and incapable of absorbing forces and deforms very rapidly. In addition, the implant is only poorly connected or anchored to the bone.

DE 10 2005 037 141 A1 discloses an implant which has an open-pore metal sponge as thermoset bone substitute. DE 32 24 265 A1 mentions a method for producing an implant in which a model from continuous open-pore material is used wherein a model material with a three dimensional grid or net structure is used.

It would therefore be desirable and advantageous to provide an improved tibia implant which is more dimensionally stable and which better grows together with the bone

SUMMARY OF THE INVENTION

According to one aspect of the present invention, a tibia implant for tightening patella tendons, includes a sponge structure and a base plate which carries the sponge structure, wherein at least parts of the sponge structure have a lattice structure, wherein the implant has a tapered vertical cross section and is insertable into a knee proximate incision of a tibia so that two sides of the sponge structure are in one to one abutting relationship with two cut surfaces of the incision.

The implant according to the invention has the significant advantage that due to the sponge structure which can have any desired pore size and is in particular open-pore, it is very dimensionally stable and can therefore absorb and support very great forces. The sponge structure preferably has a net like, in particular regular structure.

According to another advantageous feature of the present invention, the base can form a part of the circumferential support frame which encloses the sponge structure. On one hand, the circumferential support frame supports the sponge structure; on the other hand the support frame serves as stable spacer for the tibia section and holds the latter in the desired braced position so that the tendons retain their newly created tightening.

In a preferred exemplary embodiment the sponge structure has a three dimensional structure. This ensures that the support forces are conducted into the inside of the implant without causing damage to the sponge structure.

The lattice structure extends over multiple parallel planes. Even when the lattice structure has an imperfection in one plane, the stiffness and rigidity is retained because the support is supported and ensured by the further planes.

In a preferred embodiment of the tibia implant according to the invention two parallel lattice structure plane are offset by half a lattice width in the x and/or in the y axis. The lattice sections are bent between the lattice points in the direction of the lattice structure plane which is parallel to the lattice sections, so that they contact one another in their bending points. The bent lattice sections do not only define the lattice structure plane but also stiffen the latter relative to the parallel plane. A detailed description is given further below where reference is made to the drawing.

In order to fasten the implant to the bone as fast and simple as possible at least one vertical side surface of the support frame is provided with at least two projecting fastening loops. These fastening loops are configured flat so that they can support great forces in the loop plane. The fastening loops extend toward the tibia and toward the partially severed tibia section. An optimal fitting is achieved in that the fastening loops project from the support frame horizontally and/or inclined toward the horizontal. In addition, the fastening loops can have one or multiple receiving openings for fastening means such as screws or the like. A hooking engagement is also possible. A fast individual fitting of the implant to the respective bone shape is achieved in that the fastening loops protrude bendable and adjustable from the support frame.

Preferably the tibia implant according to the invention is made of metal for example stainless steel or titanium, or from plastic, for example PEEK. Alloys of the metal materials or mixtures of the plastics, also material additives such as glass fiber or carbon fiber are conceivable.

In order to facilitate the anchoring of the implant in the bone, the tibia implant has a coating which supports the attachment of bone mass by growth, for example hydroxyapatite. In addition the spikes protrude over the sponge structure These spikes penetrate into the bone surface and prevent a shifting of the tibia implant on the bone. The spikes are smaller in the region of the wedge cut and and/or protrude less out of the sponge structure than on the opposing wider end. Very high forces can be absorbed preferably in that the spikes extend from a sponge structure through the implant and its internal space to the other sponge structure and protrude outwardly over the latter so that the forces can be transferred from the tibia section directly to the tibia.

A fast growing in of the tibia implant is advantageously facilitated in that the support frame has openings. Bone mass can be introduced into the implant through the openings so that the internal space which is located between the sponge structures overgrows quickly.

An advantageous manufacturing method provides that the tibia implant is produced by means of a rapid manufacturing method. The implant can be produced in multiple sizes without major constructive changes.

Further advantages features and details of the invention follow from the sub claims and the following description in which a particularly preferred embodiment is described in detail with reference to the drawing. The features which are shown in the drawing or are mentioned in the description and/or in the claims can be relevant individually or in any combination.

BRIEF DESCRIPTION OF THE DRAWING

Other features and advantages of the present invention will be more readily apparent upon reading the following description of currently preferred exemplified embodiments of the invention with reference to the accompanying drawing, in which.

DETAILED DESCRIPTION OF PREFERRED EMBODIMENTS

Throughout all the Figures, same or corresponding elements are generally indicated by same reference numerals. These depicted embodiments are to be understood as illustrative of the invention and not as limiting in any way. It should also be understood that the drawings are not necessarily to scale and that the embodiments are sometimes illustrated by graphic symbols, phantom lines, diagrammatic representations and fragmentary views. In certain instances, details which are not necessary for an understanding of the present invention or which render other details difficult to perceive may have been omitted.

Figure 1:
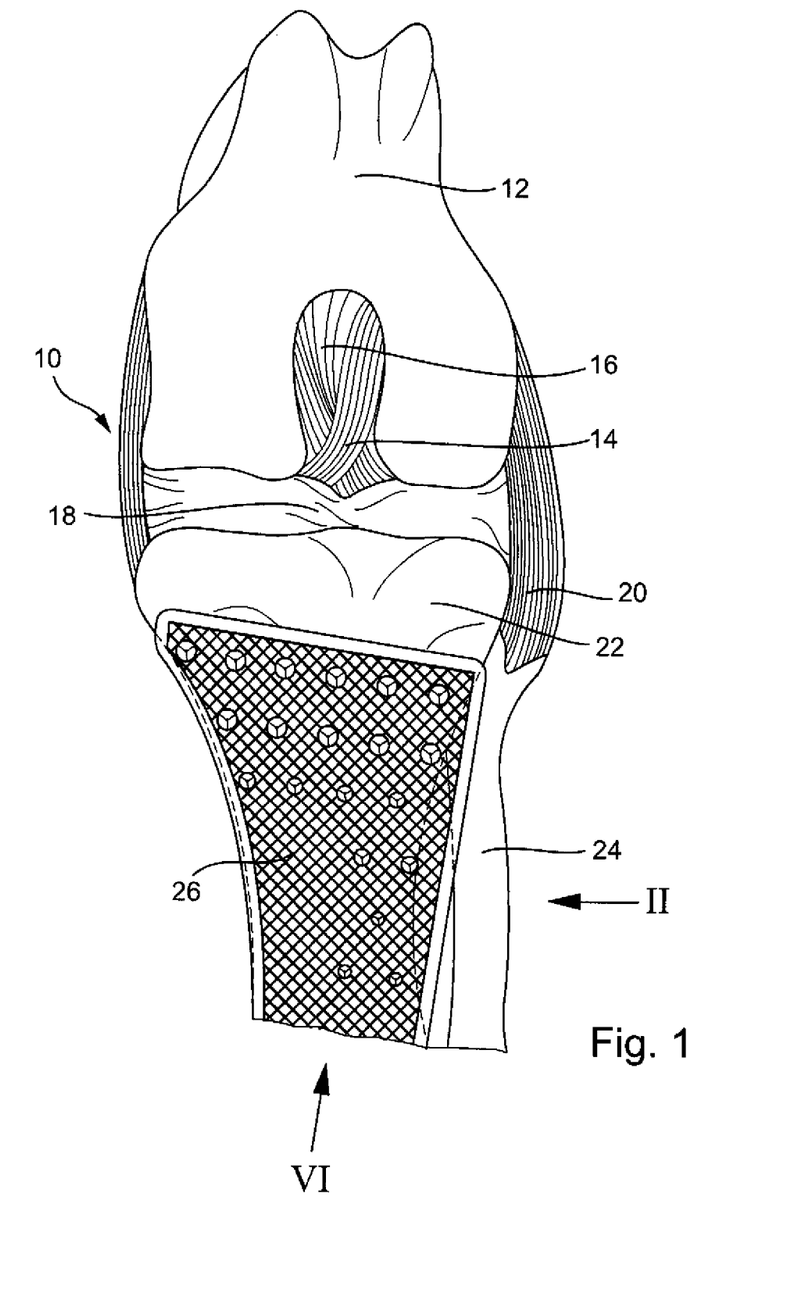
FIG. 1 shows a front view on the front side of a knee with an implant which is located in the tibia.
Figure 2:
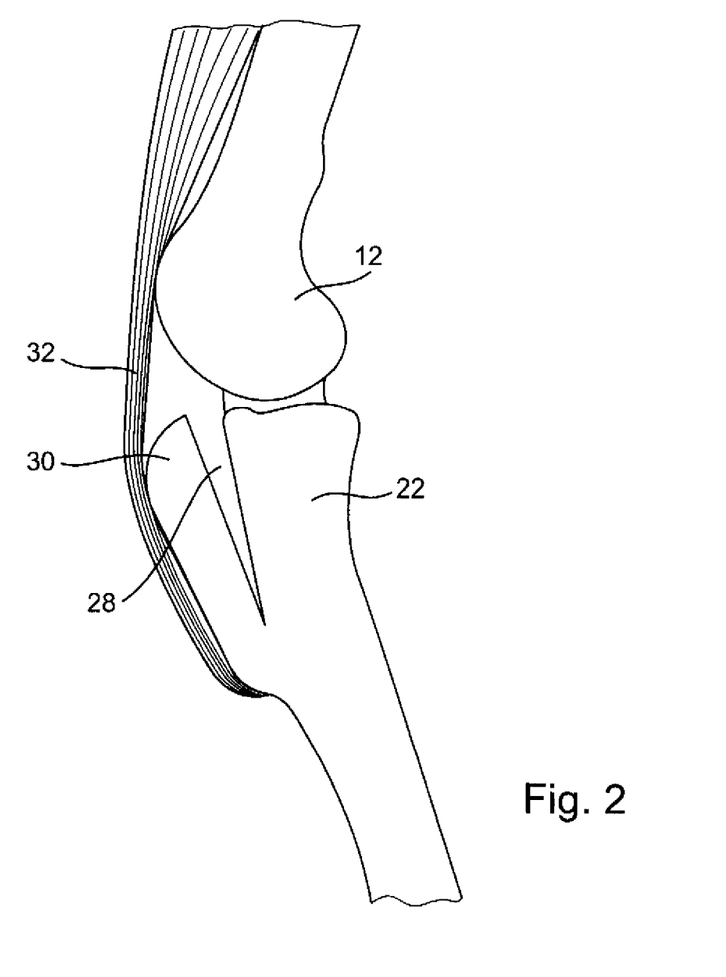
FIG. 2 shows a side view of a knee taken in the direction of the arrow II according to FIG. 1.

Turning now to the drawing, and in particular to FIG. 1, there is shown a front view onto a front side of a knee 10, in particular the lower end of the femur 12. The anterior cruciate ligament 14 and the posterior cruciate ligament 16 as well as the menisci 18 and the collateral ligament 20 are shown schematically. Beside the tibia 22, the fibula 24 can be seen. A tibia implant 26 which has an approximately trapeze shaped cross section with a concavely shaped side can be seen in the knee proximal region of the tibia 22. This tibia implant 26 is located in an incision 28 of the tibia 22 which, as can be seen in FIG. 2, is introduced into the tibia 22 essentially vertically from above so that a tibia section 30 is formed whose lower end is still connected to the tibia 22. The tibia implant 26 is inserted into this V-shaped incision 28 from the side. By bracing the tibia section 30 the anterior ligament 32 is tightened.

Figure 3:
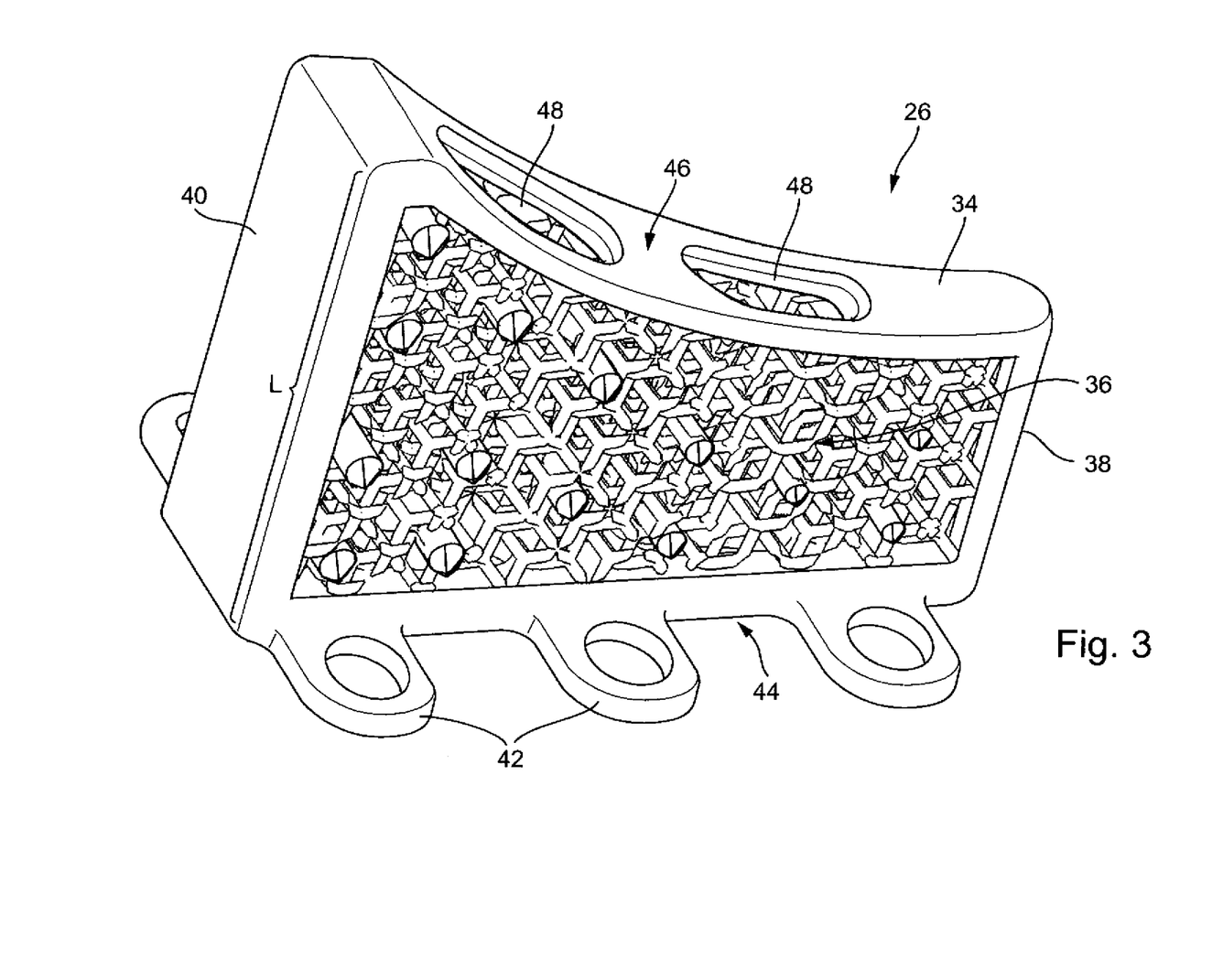
FIG. 3 shows a first perspective view of the tibia implant.

FIG. 3 shows a perspective view of the tibia implant 26 which has a circumferential support frame 34 and a sponge structure 36 located there between. The tibia implant 26 is configured wedge shaped and has a wedge edge 38. The opposing side 40 does not only have a greater width B but also a greater length L. The tibia implant 26 thus has a trapeze shape, wherein the base plate 44 which has multiple fastening loops 42 is configured even and the opposing side 46 is configured concave. In addition, it can be seen that this concave side 46 is provided with two through openings 48 through which bone material can be inserted into the inside of the tibia implant 26. In an alternative embodiment, the base plate 44 can be configured concave.

Figure 4:
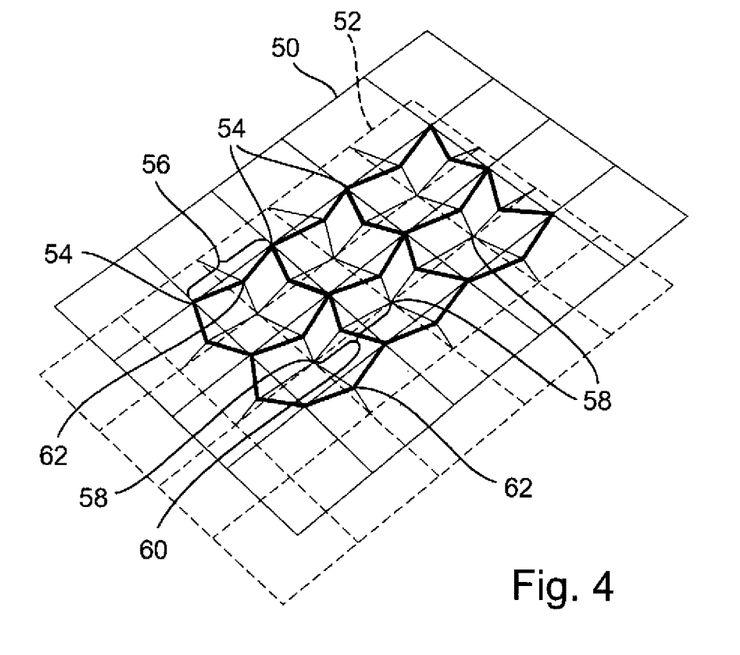
FIG. 4 shows a schematic representation of the sponge structure.

The sponge structure 36 extends over at least two planes 50 and 52 which is clearly shown in FIG. 4. The plane 50 in FIG. 4 is arranged on top and the plane 52 there underneath. In addition the lattice is shifted in the plane 50 by one lattice width in the x-direction and in the y direction. The lattice sections 56 which extend between the lattice points 54 are bent in the direction of the sponge structure which is parallel to the lattice sections i.e in the direction of the plane 52. Correspondingly the lattice sections which extend between the lattice points 58 are angled toward the sponge structure which is parallel to the lattice sections 60, i.e. in the direction of the plane 50. The lattice sections 56 and 60 contact one another in the bending sites 62. The sponge structure 36 is thus formed by a three dimensional network which has a multitude of openings, into which the bone can grow.

Figure 7A:
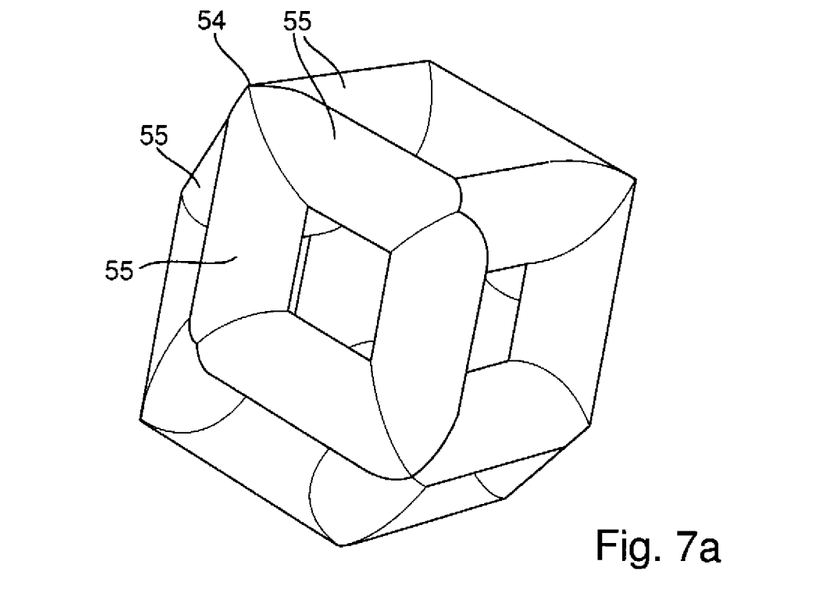
FIG. 7a shows a lattice element in perspective view.
Figure 7B:
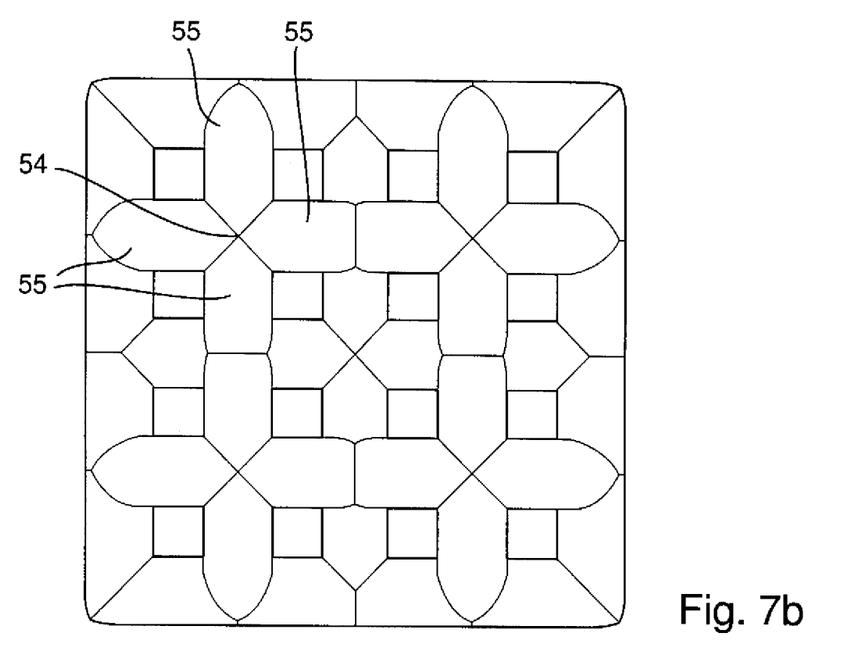
FIG. 7b shows a net constructed from multiple lattice elements

FIG. 7a shows a single lattice element, which is built between 3 planes. Four lattice rods 54 protrude at equal angular distances from the lattice point 54 towards the next parallel plane. The lattice element is formed by twelve equal lattice rods 55. In all lattice rods 55 the neutral fiber is the same. FIG. 7b shows a net which is constructed from multiple lattice elements, and which extends in the x-y plane at an angle of 90°. It is shifted in the z-plane by 45°.

Figure 5:
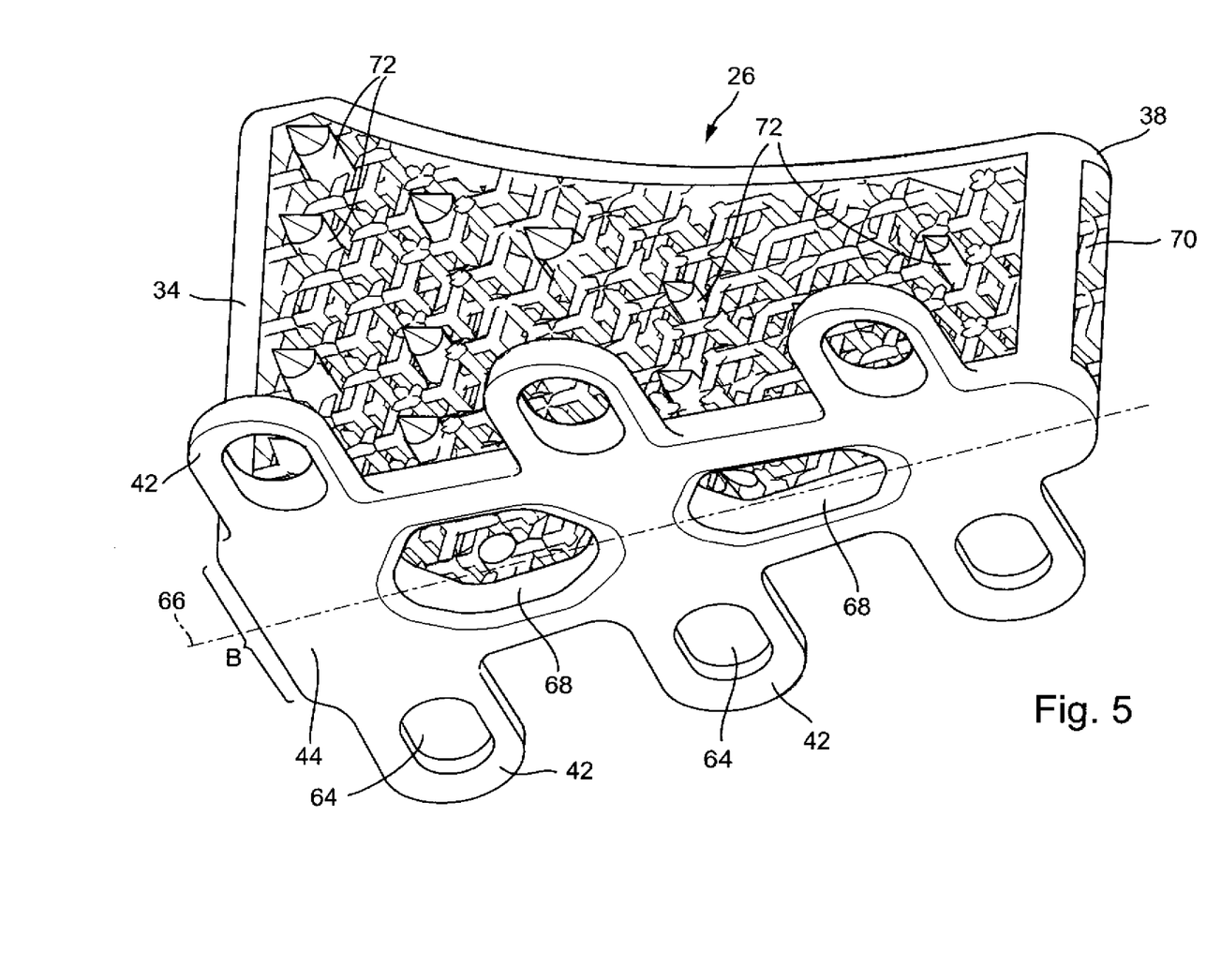
FIG. 5 shows a perspective view of the tibia implant.

FIG. 5 also shows a perspective view onto the tibia implant 26, wherein the fastening loops 42 can be clearly recognized. They protrude from the support frame 34 in the plane of the base plate 44 and each have a receiving opening 64 for a not shown fastening screw (bone screw), which is configured as oblong hole which extends transverse to the longitudinal axis 66 of the tibia implant 26. The base plate 44 is also provided with through openings 68 so that bone material can also be filled into the inside of the tibia implant through the base plate 44.

Figure 6:
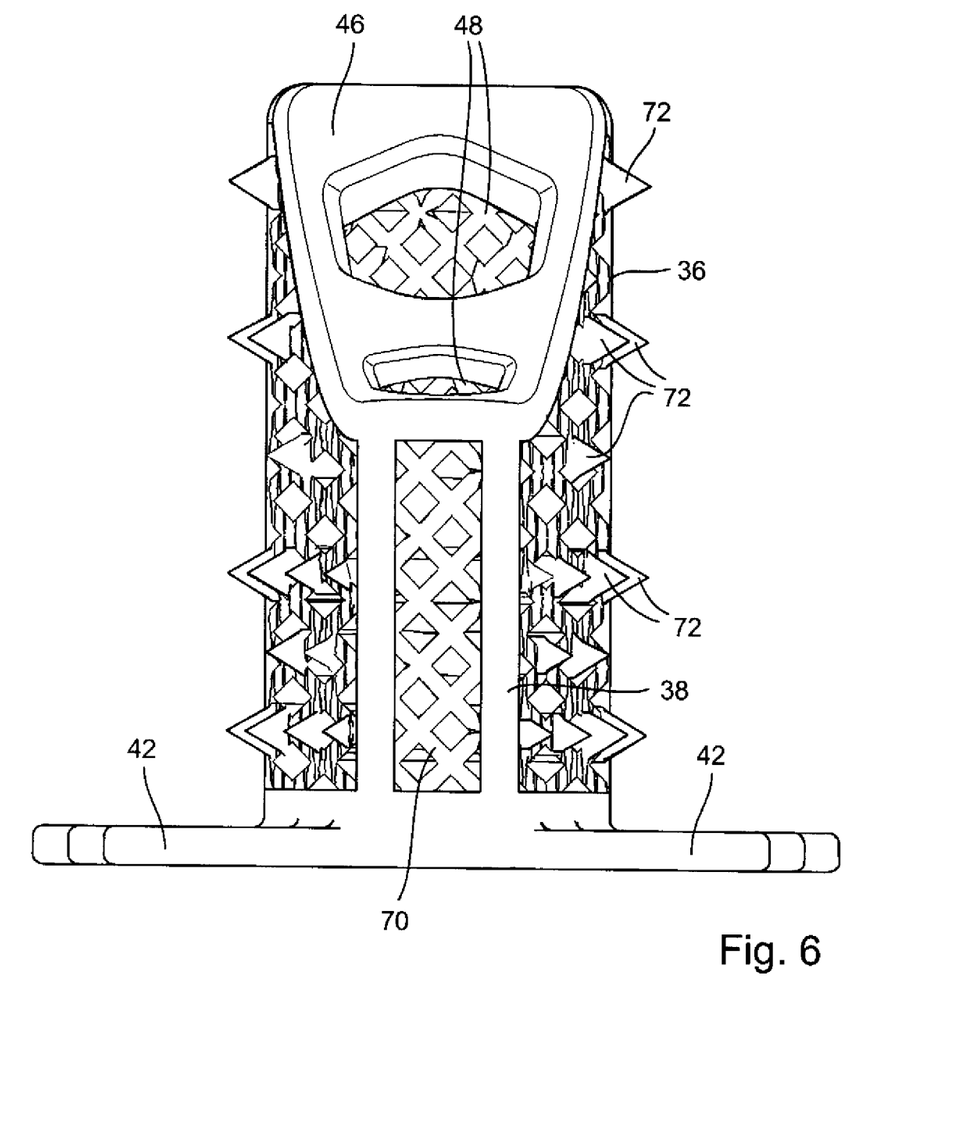
FIG. 6 shows a view taken in the direction of the arrow VI according to FIG. 1 on the cut of the tibia implant.

FIG. 6 shows the tibia implant 26 in the direction of the arrow VI according to FIG. 1 so that the through opening 70 in the wedge edge 38 can be seen clearly. This through opening 70 also serves for filling bone material into the inside of the tibia implant 26. However, spikes 72 which project out of the sponge structure 36 can also be seen which protrude over the outer contour of the tibia implant 26. These spikes 72 traverse the entire tibia implant 26 so that the forces which are introduced from the tibia section 30 are directly transferred to the tibia 22. The tibia implant 26 and in particular the sponge structure 36 is not or only minimally subjected to stress. The spikes 72 are not only shorter in the region of the wedge edge 38 but also have a smaller diameter which facilitates the insertion of the tibia implant 26 into the incision 28.

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed as new and desired to be protected by Letters Patent is set forth in the appended claims and includes equivalents of the elements recited therein:

1. A tibia implant for tightening patella tendons, comprising;
   a sponge structure; and
   a base plate, carrying the sponge structure, wherein at least parts of said sponge structure comprise a lattice structure, wherein the implant is insertable into a knee proximate incision of a tibia so that two sides of the sponge structure are in one to one abutting relationship with two cut surfaces of the incision, wherein a length dimension of the base plate extends along a longitudinal axis of the implant, and wherein the base plate is provided with at least two fastening loops projecting from the base plate transversely to the longitudinal axis of the implant and being bendable independent of each other, each of said fastening loops having an oblong fastening hole, said oblong fastening hole having a longitudinal extent which extends transversely to the longitudinal axis of the implant, and wherein the implant is tapered along the longitudinal axis in a width direction and in a thickness direction of the implant.

2. The tibia implant of claim 1, wherein the lattice structure is a regular lattice structure.

3. The tibia implant of claim 1, further comprising a circumferential support frame in surrounding relationship with the sponge structure, wherein the base plate forms a part of the circumferential support frame.

4. The tibia implant of claim 1, wherein the sponge structure is open-pored.

5. The tibia implant of claim 1, wherein the sponge structure has a three dimensional structure.

6. The tibia implant of claim 1, further comprising spikes, said spikes protruding over the sponge structure.

7. The tibia implant of claim 1, wherein the sponge structure further comprises multiple planes in parallel relationship to one another, each of said planes being formed by one of said lattice structure.

8. The tibia implant of claim 7, wherein respective neighboring ones of said multiple planes are offset relative to another by halve a lattice width along an x and/or y-axis.

9. The tibia implant of claim 8, wherein the lattice structure is formed by lattice sections and lattice points, wherein the lattice sections of the lattice structure of the respective neighboring planes are bent towards one another at bending sites between the lattice points, and wherein the respective neighboring planes contact one another at the bending sites.

10. The tibia implant of claim 1, wherein the fastening loops extend toward the tibia and toward a partially severed section of the tibia.

11. The tibia implant of claim 1, wherein the fastening loops project from the support frame in a horizontal direction or inclined relative to the horizontal direction.

12. The tibia implant of claim 1, wherein the fastening loops have one or multiple receiving openings for fasteners.

13. The tibia implant of claim 12, wherein the fasteners are screws.

14. The tibia implant of claim 1, wherein the tibia implant is made of metal or plastic.

15. The tibia implant of claim 14, wherein the metal is stainless steel or titanium.

16. The tibia implant of claim 14, wherein the plastic is PEEK.

17. The tibia implant of claim 1, further comprising a coating for supporting attachment of bone mass.

18. The tibia implant of claim 17, wherein the coating is hydroxyapatite.

19. The tibia implant of claim 3, wherein the spikes decrease in size and/or project to a decreasing extent out of the sponge structure along the implant in a direction in which the cross section is tapered.

20. The tibia implant of claim 3, wherein the spikes extend through the tibia implant from one of the two sides of the sponge structure to another one of the two sides of the sponge structure.

21. The tibia implant of claim 3, wherein the base plate or the support frame have through openings.

22. A tibia implant for tightening patella tendons, comprising:
a sponge structure; and
a base plate carrying the sponge structure and being provided with a through opening opening into the sponge structure and in flow communication with an entirety of the sponge structure, wherein at least parts of said sponge structure comprise a lattice structure, wherein the implant has a tapered vertical cross section and is insertable into a knee proximate incision of a tibia so that two sides of the sponge structure are in one to one abutting relationship with two cut surfaces of the incision,
wherein a length dimension of the base plate extends along a longitudinal axis of the implant, and wherein the implant is tapered along the longitudinal axis in a width direction and in a thickness direction of the implant.

* * * * *